(12) United States Patent
Woo et al.

(10) Patent No.: US 11,655,482 B2
(45) Date of Patent: May 23, 2023

(54) RECOMBINANT TRANSITION VECTOR FOR INCREASING FOREIGN PROTEIN EXPRESSION

(71) Applicants: OPTIPHARM CO., LTD, Chungcheongbuk-do (KR); CHUNGBUK NATIONAL UNIVERSITY INDUSTRY ACADEMIC COOPERATION FOUNDATION, Chungcheongbuk-do (KR)

(72) Inventors: Soo Dong Woo, Chungcheongbuk-do (KR); Ji Hoon Lee, Gyeonggi-do (KR); Won Seok Gwak, Chungcheongbuk-do (KR); Ji In Ma, Gyeonggi-do (KR); Beom Ku Han, Daejeon (KR); Hyun Il Kim, Seoul (KR); Charl Se Park, Chungcheongbuk-do (KR); Jae Bang Choi, Chungcheongbuk-do (KR)

(73) Assignees: OPTIPHARM CO., LTD, Chungcheongbuk-Do (KR); CHUNGBUK NATIONAL UNIVERSITY INDUSTRY ACADEMIC COOPERATION FOUNDATION, Chungcheongbuk-Do (KR)

( * ) Notice: Subject to any disclaimer, the term of this patent is extended or adjusted under 35 U.S.C. 154(b) by 548 days.

(21) Appl. No.: 16/645,386

(22) PCT Filed: Mar. 7, 2018

(86) PCT No.: PCT/KR2018/002716
§ 371 (c)(1),
(2) Date: Mar. 6, 2020

(87) PCT Pub. No.: WO2019/050111
PCT Pub. Date: Mar. 14, 2019

(65) Prior Publication Data
US 2020/0291426 A1 Sep. 17, 2020

(30) Foreign Application Priority Data
Sep. 7, 2017 (KR) .......................... 10-2017-0114614

(51) Int. Cl.
*C12N 15/86* (2006.01)
*C12N 7/00* (2006.01)
*C12P 21/00* (2006.01)

(52) U.S. Cl.
CPC .............. *C12N 15/86* (2013.01); *C12N 7/00* (2013.01); *C12P 21/00* (2013.01); *C12N 2710/14021* (2013.01); *C12N 2710/14043* (2013.01)

(58) Field of Classification Search
None
See application file for complete search history.

(56) References Cited

U.S. PATENT DOCUMENTS 6,461,863 B1 * 10/2002 Jarvis ...................... C07H 19/20
435/348

FOREIGN PATENT DOCUMENTS

KR       20120128730 A      11/2012
WO    WO-2011089271 A1 *   7/2011  ............. C12N 15/86

OTHER PUBLICATIONS

Manohar, S. L., et al., "Enhanced Gene Expression in Insect Cells and Silkworm Larva by Modified Polyhedrin Promoter Using Repeated Burst Sequence and Very Late Transcriptional Factor-1," 2010 Biotechnology and Bioengineering, 107(6), 909-916.
Acharya, A., et al., "Identification of an Enhancer-Like Element in the Polyhedrin Gene Upstream Region of Bombyx mori Nucleopolyhedrovirus," 2001 Journal of General Virology, 82(11), 2811-2819.
Liu, A., et al., "Nucleotide Sequence of a Portion of the Autographa Californica Nuclear Polyhedrosis Virus Genome Containing the EcoRI Site-Rich Region (hr5) and an Open Reading Frame Just 5' of the p10 Gene," 1986 Journal of General Virology, 67(11), 2565-2570.
Morris, T. D., et al., "Mutational Analysis of a Baculovirus Major Late Promoter," 2994 Gene, 140(2), 147-153.
Thiem, S. M., et al., "Identification, Sequence, and Transcriptional Mapping of the Major Capsid Protein Gene of the Baculovirus Autographa Californica Nuclear Polyhedrosis Virus," 1989 Journal of Virology, 63(5), 2008-2018.
Ono, C., et al., "Construction of the BmNPV T3 Bacmid System and its Application to the Functional Analysis of BmNPV he65," 2007 Journal of Insect Biotechnology and Sericology, 76(3), 161-167.
Shang, Y., et al., "Construction and Rescue of a Functional Synthetic Baculovirus," 2017 ACS Synthetic Biology, 6(7), 1393-1402.
GenBank: KY792989.1, Apr. 26, 2017.
Martinez-Solis, M., et al., "A Novel Baculovirus-Derived Promoter with High Activity in the Baculovirus Expression System," 2016 PeerJ, 4, e2183, DOI 10.7717/peerj.2183.

* cited by examiner

*Primary Examiner* — Oluwatosin A Ogunbiyi
(74) *Attorney, Agent, or Firm* — Hoffmann & Baron, LLP

(57) ABSTRACT

Disclosed are a novel recombinant transition vector for increasing expression of a foreign protein in a native form without fusion partners, and a method for mass production of a foreign target protein using the same. The recombinant transition vector according to the present disclosure may allow a large amount of a foreign target protein with a high therapeutic and prophylactic value to be expressed in an insect cell. In particular, the vector may increase the expression of the foreign target protein in an own form thereof, not fused with other fusion partners. Therefore, the use of the recombinant transition vector may produce useful proteins such as antigens in insect cells at low cost and high efficiency.

9 Claims, 4 Drawing Sheets

Specification includes a Sequence Listing.

RECOMBINANT TRANSITION VECTOR FOR INCREASING FOREIGN PROTEIN EXPRESSION

CROSS-REFERENCE TO RELATED APPLICATIONS

This application is based on and claims priority from Korean Patent Application No. 10-2017-0114614, filed on Sep. 7, 2017, with the Korean Intellectual Property Office, the disclosure of which is incorporated herein in its entirety by reference.

TECHNICAL FIELD

The present disclosure relates to a novel recombinant transition vector for increasing an expression of a foreign protein and a method for mass production of a foreign target protein using the same.

BACKGROUND

A baculovirus expression vector system (BEVS) is an expression vector system that uses a strong promoter of a nucleopolyhedrovirus (NPV) gene and has very high expression efficiency. Further, because the baculovirus expression vector system allows excellent biological and immunological activity of an expressed foreign protein by using insect cells as higher eukaryotic cells, the BEVS has a number of advantages over other expression vector systems using *E. coli*, yeast, mammal cell, etc. and has attracted much attention.

When a foreign protein is expressed in insect cells, the protein may be mass-produced to a degree similar to that in an expression system using *E. coli*, post-translational modification such as glycosylation is effectively performed, and thus a large amount of foreign proteins having a biological activity similar to that of a native protein is obtained unlike a case where *E. coli* and yeast are used as host cells. The BEVS is very useful industrially.

Meanwhile, a recombinant protein production method using mammal cells may obtain a relatively larger amount of proteins having a high therapeutic value compared to other systems. However, cultivation and maintenance of the mammal cells require a large amount of various hormones and growth regulators derived from mammals. This requires a considerable cost. However, the approach where the insect cells are used may produce recombinant proteins at low cost even when a post-translational modification similar to in the mammal cells occurs and is known to be more economical.

Currently, two expression vector systems using *Autographa californica* NPV (AcNPV) and using *Bombyx mori* NPV (BmNPV) are widely used for the production of the recombinant proteins using insect cells. However, when a foreign protein is expressed in insect cells using only a promoter of a polyhedrin gene, an amount of target proteins may be significantly low, which is pointed out as a technical limitation. It is believed that this low level of expression is mainly due to inefficient recognition of a signal sequence of a foreign gene by host cells, or is due to a decrease in a protein processing ability of the host cell due to infection of a virus. In addition, the expression of the foreign protein is carried out using a strong promoter of a polyhedrin protein coding gene. However, the expression level of the foreign protein has been reported to be smaller compared with the expression level of an original polyhedrin protein.

Meanwhile, Korean Patent KR 10-1563583 discloses a method for efficient mass production of a foreign target protein by enhancing foreign protein expression using a strong promoter of a polyhedrin protein coding gene. However, the technique of Korean Patent KR 10-1563583 relates to a technique of increasing the amount of the expression by fragmenting the polyhedrin protein into various parts and fusing the parts with the foreign protein. Thus, the foreign protein must be expressed in a fused state with the partial polyhedrin protein. When the foreign protein is expressed in this way, additional cleavage, that is, cleavage of the fused polyhedrin portion and a purification process are necessarily required for foreign protein use. In this process, there occurs a disadvantage that the foreign target protein is cut together with the fused polyhedrin portion or loses its activity. There is still a need for a new technique for easy mass production of a foreign target protein.

SUMMARY

The present inventors studied a method of increasing foreign target protein production by combining a promoter of a polyhedrin protein coding gene of baculovirus and an additional expression enhancing factor. In this study, we confirmed that when using a combination of a homologous region 5 (hr5) sequence, a burst sequence, and a vp39 promoter, an expression level of the foreign protein may be effectively increased and completed the present disclosure.

The present disclosure has been made in an effort to provide a recombinant transition vector including a combination of a promoter of a polyhedrin protein coding gene of baculovirus, a burst sequence represented by SEQ ID NO: 2 operably linked to the promoter, a hr5 (homologous region 5) sequence represented by SEQ ID NO: 1, and a vp39 promoter represented by SEQ ID NO: 3, and to provide a method for mass production of a foreign target protein using the same.

An exemplary embodiment of the present disclosure provides a recombinant transition vector including a) a promoter of a polyhedrin protein coding gene of baculovirus; and b) a burst sequence represented by SEQ ID NO: 2 and operably linked with the promoter.

Further, the recombinant transition vector further includes at least one sequence selected from a group consisting of c) a hr5 (homologous region 5) sequence represented by SEQ ID NO: 1, and a vp39 promoter represented by SEQ ID NO: 3.

Further, another exemplary embodiment of the present disclosure provides a recombinant transition vector including a) a vp39 promoter represented by SEQ ID NO: 3; and b) a promoter of a polyhedrin protein coding gene of baculovirus.

Further, the recombinant transition vector further includes c) a hr5 (homologous region 5) sequence represented by SEQ ID NO: 1.

Further, yet another exemplary embodiment of the present disclosure provides an insect cell into which the recombinant transition vector has been introduced.

Further, yet another exemplary embodiment of the present disclosure provides a mass production method of a foreign target protein, the method including a) cloning a foreign target protein coding nucleotide sequence into the recombinant transition vector; and b) introducing the cloned recombinant transition vector and a bacmid into an insect cell.

According to the exemplary embodiments of the present disclosure, the recombinant transition vector may allow a large amount of a foreign target protein with a high therapeutic value to be expressed in an insect-based expression system. In particular, the vector may increase the expression of the foreign target protein in an own form thereof, not fused with other proteins. Therefore, the use of the recombinant transition vector according to the present disclosure may produce useful proteins such as antigens in insects and insect cells at low cost and high efficiency.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

The present disclosure provides a recombinant transition vector, an insect cell into which the vector is introduced, and a method for mass production of a foreign target protein using the vector.

The recombinant transition vector according to the present disclosure includes a combination of a promoter of a polyhedrin protein coding gene of baculovirus and a homologous region 5 (hr5) sequence, a burst sequence, and a vp39 promoter. Thus, the foreign target protein may be mass-produced in an own form of the target protein rather than in a fused form.

The present disclosure is described in more detail below.

The present disclosure provides a recombinant transition vector including a combination of a) a promoter of a polyhedrin protein coding gene of baculovirus; and b) a burst sequence represented by SEQ ID NO: 2 and operably linked with the promoter. The recombinant transition vector may be referred to as "pPol-5-EGFP" in the present disclosure.

As used herein, the term "promoter" means a minimum sequence sufficient to induce transcription.

As used herein, the phrase "promoter of a polyhedrin protein coding gene of baculovirus" may be represented by SEQ ID NO: 4. The promoter of the polyhedrin protein coding gene of baculovirus refers to a promoter which is located in front of a foreign target protein and may increase expression efficiency of the target protein. The promoter of the polyhedrin protein coding gene of baculovirus refers to a DNA sequence essential for transcription and functional expression of the polyhedrin protein. Preferably, the promoter of the polyhedrin protein coding gene of baculovirus may include about upstream-100 bp sequence region, more preferably, upstream-1 bp to upstream-52 bp region of a structural gene of *Autographa californica* NPV (AcNPV) polyhedrin protein.

As used herein, the term "baculovirus" includes all insect-based pathogenic viruses that are not pathogenic to humans or vertebrates and that are pathogenic to insects only. Preferably, the baculovirus may include nucleopolyhedrovirus (NPV) and granulovirus (GV). In one example of the present disclosure, the baculovirus may include nucleopolyhedrovirus (NPV).

As used herein, the term "polyhedrin protein of baculovirus" refers to a structural protein of a baculovirus polyhedrin that is synthesized in large quantities from the nucleus of insect cells at an end of infection. For example, the polyhedrin protein of baculovirus may refer to a polyhedrin protein of *Autographa californica* nucleopolyhedrovirus (AcNPV), a polyhedrin protein of *Spodoptera exigua* NPV, a polyhedrin protein of *Bombix mori* NPV, etc. Preferably, the polyhedrin protein of baculovirus may refer to a polyhedrin protein of *Autographa californica* nucleopolyhedrovirus (AcNPV).

As used herein, the burst sequence refers to a portion present in the polyhedrin promoter and to a sequence located between a translation initiation site and TAAG. At the end of baculovirus infection, VLF-1 (very late expression factor-1) is known to specifically bind to the burst sequence to promote transcription (Manohar et al. 2010). The burst sequence according to the present disclosure may be a base sequence represented by SEQ ID NO: 2 or a variant thereof.

The recombinant transition vector including the promoter of the baculovirus polyhedrin protein coding gene and the burst sequence represented by SEQ ID NO: 2 operably linked to the promoter according to the present disclosure may be the simplest type of the recombinant transition vector that may increase the expression of the foreign target protein most efficiently. Based on the recombinant transition vector, additional promoters or promotion sequences may be used in combination.

Thus, the present disclosure provides the recombinant transition vector further including at least one sequence selected from a group consisting of the hr5 (homologous region 5) sequence represented by SEQ ID NO: 1 and the vp39 promoter represented by SEQ ID NO: 3.

The hr (homologous region) sequence means a repeated base sequence region present in the baculovirus genome, and the hr may include hr1, hr2L, hr2R, hr3, hr4L, hr4R, and hr5. Most of these hr sequences play an important role in viral DNA replication and propagation and function as transcriptional promoters of viral or nonviral genes. In accordance with the present disclosure, the hr5 sequence is used, which may be a base sequence represented by SEQ ID NO: 1 or a variant thereof.

Further, the vp39 promoter refers to a promoter that controls the expression of the vp39 gene, and the vp39 gene is a late gene and is one of structural proteins of a virus particle. The vp39 promoter may be a base sequence represented by SEQ ID NO: 3 or a variant thereof.

In accordance with the present disclosure, as long as the promoter of the polyhedrin protein coding gene of the baculovirus, the burst sequence represented by SEQ ID NO: 2, the hr5 (homologous region 5) sequence represented by SEQ ID NO: 1, and vp39 promoter represented by SEQ ID NO: 3 increase the expression of the foreign target protein, the order, number, and orientation thereof may be appropriately adjusted and used according to common knowledge of those skilled in the art.

In one preferred example of the present disclosure, in the recombinant transition vector, the hr5 sequence represented by SEQ ID NO: 1, the promoter of the polyhedrin protein coding gene of baculovirus, and the burst sequence represented by SEQ ID NO: 2 are sequentially linked to each other; the hr5 sequence represented by SEQ ID NO: 1, the vp39 promoter represented by SEQ ID NO: 3, the promoter of the polyhedrin protein coding gene of baculovirus, and the burst sequence represented by SEQ ID NO: 2 are sequentially linked to each other; alternatively, the vp39 promoter represented by SEQ ID NO: 3, the promoter of the polyhedrin protein coding gene of baculovirus, and the burst sequence represented by SEQ ID NO: 2 are sequentially linked to each other. The present disclosure is not limited thereto, and the vector may include additional promoters or sequences for promoting expression.

As used herein, the recombinant transition vectors may be referred to as "pPol-4-EGFP", "pPol-1-EGFP", and "pPol-3-EGFP" respectively.

Further, the present disclosure provides a recombinant transition vector including a) the vp39 promoter represented by SEQ ID NO: 3; and b) the promoter of the polyhedrin protein coding gene of baculovirus. This vector may be referred to as "pPol-6-EGFP" in the present disclosure. The pPol-6-EGFP does not include the burst sequence represented by SEQ ID NO: 2. However, in order to further promote the expression of the foreign target protein by the polyhedrin protein coding gene promoter, the vector may be characterized by including the vp39 promoter represented by SEQ ID NO: 3.

The vp39 promoter represented by SEQ ID NO: 3 and the promoter of the polyhedrin protein coding gene of baculovirus may be linked to each other in an interchangeable order. Preferably, the vp39 promoter and the promoter of the polyhedrin protein coding gene of baculovirus may be sequentially linked to each other.

Further, the present disclosure provides a recombinant transition vector characterized by further including the hr5 (homologous region 5) sequence represented by SEQ ID NO: 1 in the above recombinant transition vector. This vector may be referred to as "pPol-2-EGFP" in the present disclosure.

As long as the hr5 (homologous region 5) sequence represented by SEQ ID NO: 1, the vp39 promoter represented by SEQ ID NO: 3, and the promoter of the polyhedrin protein coding gene of baculovirus may achieve increased expression of the foreign target protein, the order, number and orientation thereof may be appropriately adjusted and used according to common knowledge of those skilled in the art. Preferably, the hr5 (homologous region 5) sequence, the vp39 promoter and the promoter of the polyhedrin protein coding gene of baculovirus are sequentially linked to each other.

Figure 1:
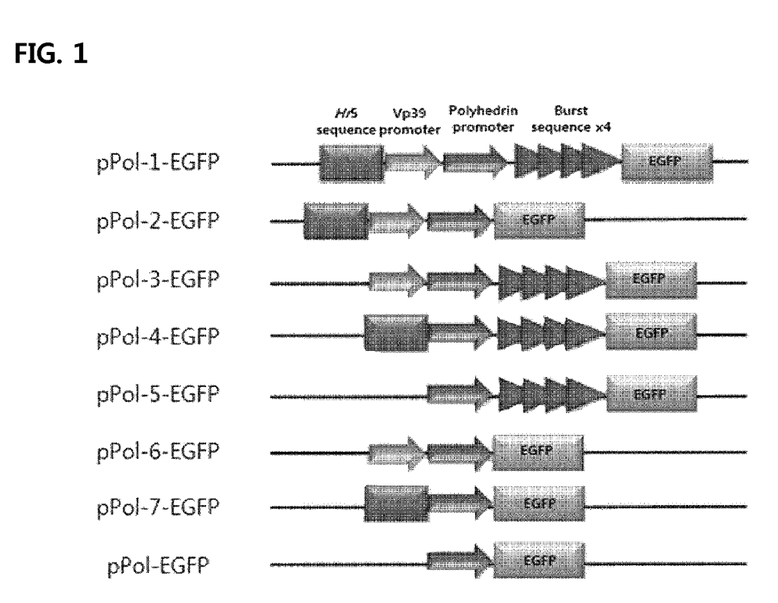
FIG. 1 is a schematic representation of a recombinant transition vector according to the present disclosure and pPol-EGFP as Comparative Example.

In accordance with the present disclosure, the recombinant transition vector may have a cleavage map as shown in FIG. 1. As long as the composition of the vector capable of achieving increased expression of the foreign target protein according to the present disclosure, the composition thereof is not limited thereto.

As used herein, variants of base sequences refer to functional equivalents of a nucleic acid molecule. That is, in the variants of base sequences, some base sequences have been modified by deletion, substitution or insertion, but the variants may act functionally the same as the existing nucleic acid molecules. Such variants may include base sequences having a sequence homology of at least 70%, more preferably at least 80%, even more preferably at least 90%, and most preferably at least 95% with existing base sequences. The "% of sequence homology" with the polynucleotide may be identified by comparing a comparison region with two optimally arranged sequences. Some of the polynucleotide sequences in the comparison region may include an addition or deletion (i.e., gap) as compared to a reference sequence (not including an addition or deletion) for the optimal arrangement of the two sequences.

As used herein, when a coding gene of a target polypeptide to be expressed is operably linked to the recombinant vector, the "recombinant vector" may be used as an expression vector of a target polypeptide capable of expressing the target polypeptide at high efficiency in an appropriate host cell. The recombinant vector may be expressible in the host cell.

As used herein, the phrase "operably linked" refers to a functional link between a nucleic acid expression control sequence and a nucleic acid sequence encoding a protein of interest to perform a general function. For example, a promoter and a nucleic acid sequence encoding a protein or RNA may be operably linked to each other to affect expression of the coding sequence. The operative linkage with the recombinant vector may be prepared using genetic recombining techniques well known in the art. A site-specific DNA cleavage and ligation uses enzymes and the like commonly known in the art.

Further, the present disclosure provides an insect cell incorporating the recombinant transition vector according to the present disclosure therein.

The insect cell according to the present disclosure may include one insect cell selected from a group consisting of BT1-Tn-5B1-4 or Hi5 (High Five™) cells of *Tricopluscia ni*, LD652Y cells of *Lymantria dispar*, Sf9 cells of *Spodoptera frugiperda*, Sf21 cells of *Spodoptera frugiperda*, Kc1 cells of *Drosophila*, SL2 cells of *Drosophila*, Bmb5 (*Bombyx mori* 5) cells and mosquito cells. Preferably, the insect cell may be one insect cell selected from a group consisting of Sf9, Sf21, Hi5 and Bm5, but is not limited thereto.

As used herein, the insect cell may be used interchangeably in the sense that includes all insects including the insect cell.

As used herein, "introduction" means transplantation of a certain DNA from outside into a cell. In other words, when a DNA as a kind of nucleic acid extracted from a cell of one line of an organism (except a viral cell) is injected into a living eukaryotic cell of another line, the DNA enters the cell and changes a genotype thereof. This may be referred to as the introduction. In other words, the "introduction" refers to introducing a specific gene into a host cell to be expressed in the host cell.

A method for introducing the recombinant vector according to the present disclosure into a cell line may include methods known in the art, such as calcium phosphate coprecipitation, DEAE-dextran treatment, electroporation, and redistribution.

Further, the insect cell according to the present disclosure may contain bacmid introduced thereto at the same time of the introduction of the vector.

As used herein, the term "bacmid" refers to a compound word between baculovirus and plasmid, which means a baculovirus shuttle vector. In accordance with the present disclosure, the bacmid may include ApGOZA and AcGOZA based on AcNPV, BpGOZA based on BmNPV (*Bombyx mori* nucleopolyhedrovirus) (see int J. indust Entomol Vol.

2. No. 2001, pp 155 to 160), and BmGOZA based on BmNPV (see Biotechnology Letters 23: 1809-1817, 2001) genomes without limitation. Preferably, the bacmid may be based on AcNPV (*Autographa californica* nucleopolyhedrovirus).

Further, the present disclosure may provide a mass production method of a foreign target protein. The method may include a) cloning a foreign target protein coding nucleotide sequence into the recombinant transition vector according to the present disclosure; and b) introducing the cloned recombinant transition vector and bacmid into an insect cell.

According to the method for mass production of the foreign target protein according to the present disclosure, the target foreign protein may be obtained in an insect cell in an amount of about 2 to 3 times more than an amount in a conventional technique using only the promoter of the polyhedrin protein coding gene of baculovirus.

As used herein, the target protein may include, for example, a hormone, a hormone analog, an enzyme, an enzyme inhibitor, a signaling protein or part thereof, an antibody or part thereof, a short chain antibody, a binding protein or a binding domain, an antigen, an attachment protein, a structural protein, a regulatory protein, a toxin protein, cytokine, a transcriptional regulator, a blood coagulation factor, or vaccine protein. The present disclosure is not limited thereto.

Overlapping content is omitted in consideration of complexity of the present specification. Terms not otherwise defined herein have meanings commonly used in the technical field to which the present disclosure belongs.

Hereinafter, the present disclosure will be described in detail based on examples. However, following examples are merely illustrative of the present disclosure and thus, contents of the present disclosure are not limited to the following examples.

Present Example 1

Construction of Recombinant Transition Vector with Improved Expression Efficiency To construct the recombinant vector with improved expression efficiency, a homologous region 5 (hr5) sequence (SEQ ID NO: 1) as reported as a transcriptional promoter in addition to the polyhedrin gene promoter (SEQ ID NO: 4), a burst sequence (SEQ ID NO: 2) to increase the protein expression level, and a vp39 promoter (SEQ ID NO: 3) to enhance the expression level as another promoter were used Enhanced green fluorescent protein (EGFP) was used as a marker protein to identify protein overexpression by the polyhedrin gene promoter. Vectors having various combinations thereof as produced are shown in Table 1 and FIG. 1.

As shown in Table 1 and FIG. 1, various combinations of the hr5 sequence, vp39 promoter, burst sequence, based on the polyhedrin gene promoter were named pPol-1-EGFP, pPol-2-EGFP, pPol-3-EGFP, pPol-4-EGFP, pPol-5-EGFP, pPol-6-EGFP, and pPol-7-EGFP. In a comparative example, pPol-EGFP was constructed and used to express only an EGFP gene downstream of the promoter of the polyhedrin protein coding gene.

Specifically, for the preparation of the baculovirus transition vector containing a combination of the transcription enhancer, that is, the VP39 promoter, and the polyhedrin gene promoter, the VP39 promoter-polyhedrin gene promoter-burst sequence×4 as synthesized was cloned into a pHIP vector. Clontech (Lonza, USA) (SEQ ID NO: 9) was used as a transition vector, and the vector is a vector in which an MCS exists between an ORF603 region and an ORF1629 region. The sequences shown in FIG. 1 were cloned into MSCs. EGFP was obtained by restriction enzyme treatment using a T & A cloning vector cloned with a GFP gene. Then, the EGFP was cloned into the prepared vector to prepare pPol-1-EGFP. Six different transition vectors were produced via self-ligation after restriction enzyme treatment from the EGFP-cloned transition vectors. Whether all transition vectors were cloned with EGFP was finally examined using restriction enzyme treatment and base sequence analysis.

Present Example 2

Construction of Recombinant Virus Having Vector Introduced Thereto

Figure 2:
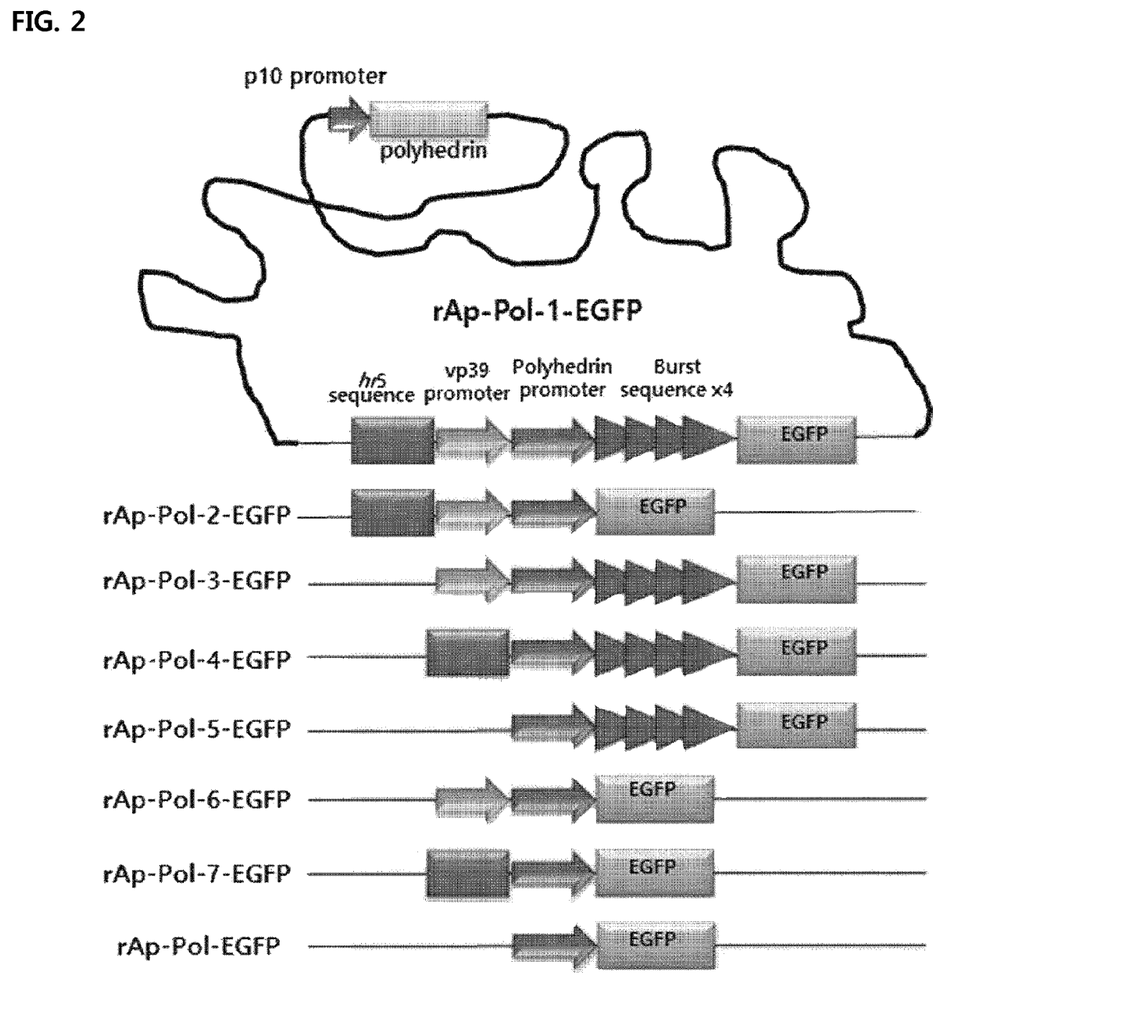
FIG. 2 shows a schematic representation of a structure of a recombinant virus into which a recombinant transition vector in accordance with the present disclosure is introduced.

In order to construct a recombinant virus having a recombinant vector prepared in Present Example 1 introduced thereto, the recombinant transition vector DNA of the present Example 1 and ApGOZA DNA (see Je et al., Int. J. Indust. Entomol., 2: 155-160 (2001)) as bacmid of AcNPV were co-introduced into an insect cell line Sf9 (*Spodoptera frugiperda* 9) (Gibco BRL, USA), thereby to construct recombinant viruses via homologous recombination between DNAs. A structure of the recombinant virus as produced is shown in FIG. 2. The recombinant viruses were indicated as rAP-pPol-1-EGFP, rAP-pPol-2-EGFP, rAP-pPol-3-EGFP, rAP-pPol-4-EGFP, rAP-pPol-5-EGFP, rAP-pPol-6-EGFP, rAP-pPol-7-EGFP and rAP-pPol-EGFP respectively.

Specifically, for the production of the recombinant virus, 500 ng of the recombinant transition vector prepared in Present Example 1 and 100 ng of bApGOZA DNA (Je et al., 2001) were mixed with 100 µl of Grace's Insect Medium (unsupplemented) (Invitrogen, USA). 8 µl of Cellfectin® II Reagent (Invitrogen, USA), a transfection reagent was added to 100 µl of Grace's Insect Medium (unsupplemented) (Invitrogen, USA). Both mixtures were mixed with each

TABLE 1

| Vector name | Recombinant sequence |
| --- | --- |
| pPol-1-EGFP | hr5 sequence-vp39 promoter-polyhedrin promoter-burst sequence-EGFP |
| pPol-2-EGFP | hr5 sequence-vp39 promoter-polyhedrin promoter-EGFP |
| pPol-3-EGFP | vp39 promoter-polyhedrin promoter-burst sequence-EGFP |
| pPol-4-EGFP | hr5 sequence-polyhedrin promoter-burst sequence-EGFP |
| pPol-5-EGFP | polyhedrin promoter-burst sequence-EGFP |
| pPol-6-EGFP | vp39 promoter-polyhedrin promoter-EGFP |
| pPol-7-EGFP | hr5 sequence-polyhedrin promoter-EGFP |
| pPol-EGFP | polyhedrin promoter-EGFP | other and were reacted at 27° C. for 30 minutes. The mixture after the reaction has been completed was transfected into Sf9 cells dispensed at $1.0 \times 10^6$ cells/ml. After three days since the transfection, the production of the recombinant virus was checked using a phase difference microscope.

After pure separation of the recombinant viruses as produced, presence or absence of a target sequence and a purity of the virus were identified via PCR amplification. Purification of the recombinant virus was performed by a plaque assay method. We dispensed Sf9 cells into a 60 mm dish (SPL Co. Ltd., Korea) at $2.0 \times 10^6$ cells/ml and diluted a cell culture medium in which the recombinant virus production was confirmed at $10^{-3}$ to $10^{-5}$ and incubated for 4 hours. Subsequently, the preparation of agarose was carried out by sterilizing and dissolving 5% SeaPlaque Agarose (Lonza, USA), and then being allowed to stand in a 45° C. water bath and then being mixed with the cell culture medium to finally prepare 0.5% agarose. After virus transfection thereto for 4 hours, the inoculum was completely removed and the prepared agarose gel was overlaid on the infected cells by 3 ml and incubated at 27° C. Presence or absence of plaque was observed after 3 days. The produced plaques were separated therefrom using a micropipette and were added to 100 μl of the cell culture medium, and vortexed. The thus mixed solution was transfected into a 24 well plate in which Sf9 cells were $1.0 \times 10^4$ cells/ml dispensed. After 3 days of the transfection, the cells for which the recombinant virus production was confirmed were collected. Viral DNA was extracted therefrom. Then, PCR thereof was performed to identify the purity of the recombinant virus. The PCR to check the purity of the virus was performed as follows: an insertion was checked using a specific primer 5'-GGT ACC ATA TAT AGT TGC TGA TGG GA-3' (SEQ ID NO: 5) and a EGFP gene specific primer 5'-GAG CTC TTA CTT GTA CAG CTC GTC C-3' (SEQ ID NO: 6) in an ORF603 region upstream of a location in which the target gene is transitioned by five terminals. Deletion of a parental virus bApGOZA was checked via amplification of the mini-F gene present only in ApGOZA virus. This was checked using a mini-F specific F-primer 5'-ATG TTC AGA ATG AAA CTC ATG GAA-3' (SEQ ID NO: 7) and a mini-F specific R-primer 5'-TTA TCT AAT CTC CCA GCG TGG TT-3' (SEQ ID NO: 8). The results are shown in FIG. 3.

Figure 3:
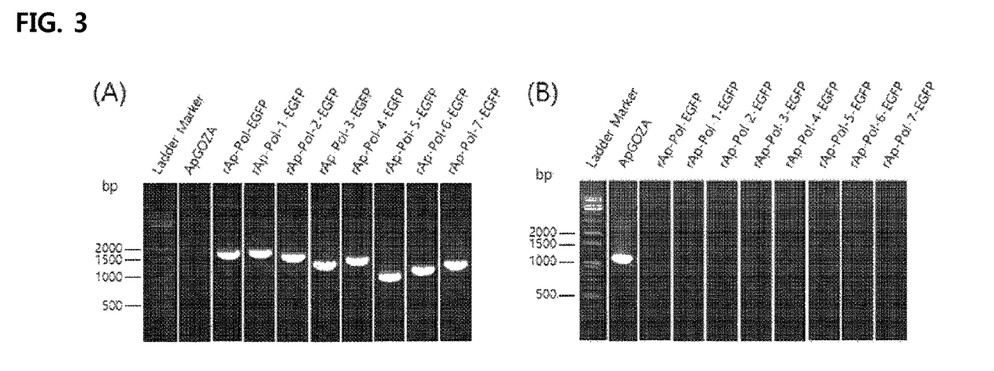
FIG. 3 shows a result (A) of confirmation of generation of recombinant baculovirus using the recombinant transition vector in accordance with the present disclosure by PCR amplifying of a target gene EGFP, and a result (B) of confirmation of purity of generated recombinant baculovirus by PCR amplifying of a mini-F gene present only in ApGOZA virus.

As shown in FIG. 3, each recombinant virus showed an amplification product of the target sequence EGFP at a predicted location (FIG. 3(A)). Further, the amplification of the mini-F gene present only in ApGOZA virus did not occur, thus confirming a purity thereof (FIG. 3(B)). In other words, according to the recombinant virus according to the present disclosure, only the target gene is amplified, and the DNA of the virus used as the vector is not amplified, so that only the expression of the target gene may be purely amplified.

Present Example 3

Verification of Protein Overexpression by Recombinant Vector

In order to identify whether the purpose of enhancing the expression of the target protein is effectively achieved by the recombinant virus into which the recombinant vector is introduced, the expression of the reporter protein EGFP was observed under a fluorescence microscope. In order to investigate the expression level of the recombinant protein over time, the recombinant virus was transfected into $1.0 \times 10^6$ cells/ml of Sf21 cells at 1 MOI (multiplicity of infections). Cells were harvested at 24 h intervals from 2 to 5 days and used for fluorescence protein expression analysis. A green fluorescent protein EGFP has the highest excitation wavelength at 488 nm and the highest emission wavelength at 510 nm. Blue light (Max 470 nm) emitted from the fluorescence microscope was converted into green light (510 nm) to observe the fluorescence. After the fluorescence microscopy-based observation, the expressed fluorescence and normal cell images were taken using the INFINITY software program. The results are shown in FIG. 4.

Figure 4:
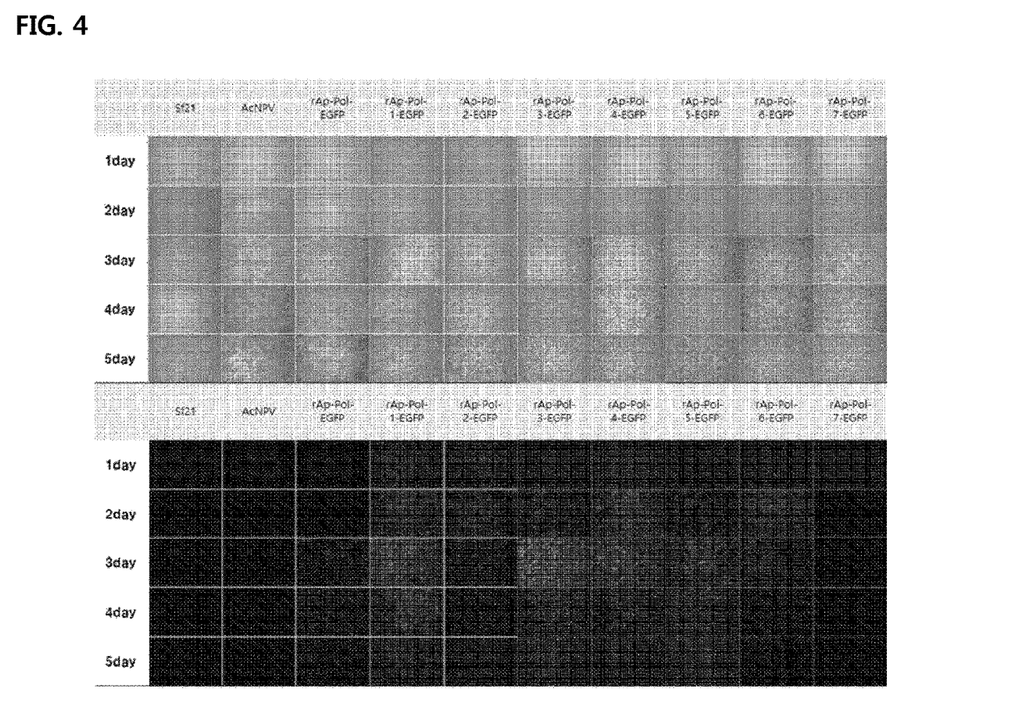
FIG. 4 shows a fluorescence microscopy-based observation result of expression of the target protein EGFP at 1 to 5 days post-infection using the recombinant transition vector in accordance with the present disclosure.

As shown in FIG. 4, the expression level of the target protein varies according to the type of the recombinant vector. The comparative example, rAp-Pol-EGFP showed the lowest level of fluorescence. The stronger fluorescence was exhibited in the vector having the combination of the promoter of the polyhedron protein coding gene and the additional promoter and expression promotion sequence. The highest increase in the protein expression was observed in rAp-Pol-1-EGFP, rAp-Pol-3-EGFP, rAp-Pol-4-EGFP, and rAp-Pol-5-EGFP.

In addition, the effect of increasing the expression level of various types of Present Examples over Comparative Example was measured using a fluorescence photometer. To analyze the expression level of each recombinant fused protein, after transfecting the recombinant virus into Sf21 cells of $1.0 \times 10^6$ cells/ml at 1 MOI, cells were harvested after 3 days. Thereafter, the cells were collected by cold centrifugation at 4° C. for 5 minutes at 1000×g and were washed with phosphate buffed saline (PBS). 900 μl of RIPA buffer (20 mM Tris-HCl pH 7.5, 50 mM NaCl, 5% Glycerol, 1 mM EDTA, 1% NP-40, 0.1% SDS) was added to precipitated cells. After crushing the cells in 3 repetitions of a process of 10 s on and 30 s off using an ultrasonic crusher, 100 μl of 1 M sodium carbonate was added thereto and the crushed cells were treated therewith for 1 hour at 37° C. and then 2 ml of PBS was added thereto. At least 3 ml of a test sample was used. A fluorescence intensity was measured using a K2™ fluorescence spectrometer (ISS Inc., USA) under an excitation filter of 450 nm and an emission filter of 510 nm. The results are shown in FIG. 5.

Figure 5:
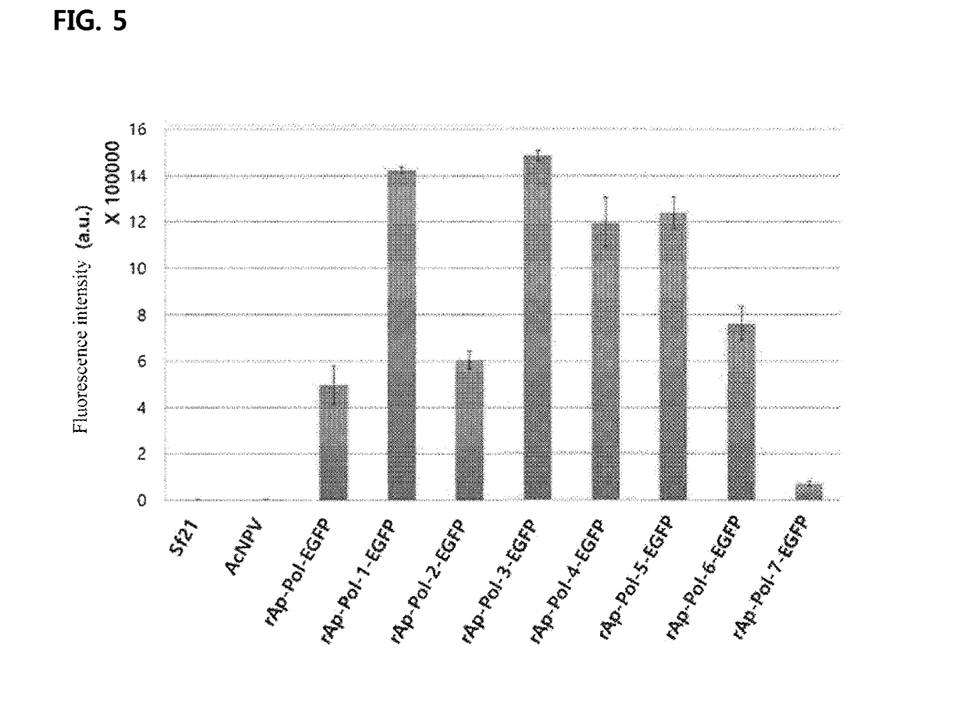
FIG. 5 shows a result of fluorescence intensity of the target protein EGFP at 3 days post-infection using the recombinant transition vector in accordance with the present disclosure.

As shown in FIG. 5, in rAp-Pol-1-EGFP, rAp-Pol-3-EGFP, rAp-Pol-4-EGFP, and rAp-Pol-5-EGFP, the expression level was increased by about 2 to 3 times, compared with the Comparative Example using the polyhedrin protein promoter alone. All of the selected vectors include the burst sequence. Thus, it was confirmed that the burst sequence among the single factors induces the highest protein expression effect. Further, rAp-Pol-3-EGFP having the combination of the burst sequence and vp39 promoter showed the highest expression level synergy. In another example, rAp-Pol-4-EGFP including the hr sequence and burst sequence showed a high expression level increase. However, in rAp-Pol-7-EGFP which additionally contains only the vp39 promoter without the burst sequence, the fluorescence expression was lower than that of the Comparative Example. This may indicate that the expression level of the target protein may vary depending on the combination of the transcriptional promoter and the promoter.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

INCORPORATION OF SEQUENCE LISTING

Incorporated herein by reference in its entirety is the Sequence Listing for the above-identified Application. The Sequence Listing is disclosed on a computer-readable ASCII text file titled "Sequence_Listing_2841-2_PCTUS.txt", created on Mar. 6, 2020. The sequence.txt file is 10 KB in size.

What is claimed is:

1. A recombinant transition vector comprising:
   a) a promoter of a polyhedrin protein coding gene of baculovirus;
   b) a burst sequence represented by SEQ ID NO: 2 and operably linked to the promoter; and
   c) a hr5 (homologous region 5) sequence represented by SEQ ID NO: 1;
   wherein the hr5 sequence represented by SEQ ID NO: 1, the promoter of the polyhedrin protein coding gene of baculovirus, and the burst sequence represented by SEQ ID NO: 2 are sequentially linked to each other.

2. The recombinant transition vector of claim 1, wherein the vector further includes a vp39 promoter represented by SEQ ID NO: 3, wherein the hr5 sequence represented by SEQ ID NO: 1, the vp39 promoter represented by SEQ ID NO: 3, the promoter of the polyhedrin protein coding gene of baculovirus, and the burst sequence represented by SEQ ID NO: 2 are sequentially liked to each other.

3. A recombinant transition vector comprising:
   a) a vp39 promoter represented by SEQ ID NO: 3;
   b) a promoter of a polyhedrin protein coding gene of baculovirus; and
   c) an hr5 (homologous region 5) sequence represented by SEQ ID NO: 1.

4. The recombinant transition vector of claim 3, wherein the hr5 (homologous region 5) sequence represented by SEQ ID NO: 1, the vp39 promoter represented by SEQ ID NO: 3, and the promoter of the polyhedrin protein coding gene of baculovirus are sequentially linked to each other.

5. An insect cell into which the recombinant transition vector of claim 1 is introduced.

6. The insect cell of claim 5, wherein the insect cell includes one selected from a group consisting of a BT1-Tn-5B1-4 cell, a Hi5 cell, a LD652Y cell, a Sf9 cell, a Sf21 cell, a Kc1 cell, a SL2 cell, a Bm5 cell and a mosquito cell.

7. The insect cell of claim 5, wherein bacmid is introduced to the insect cell at the same time of the introduction of the recombinant transition vector.

8. The insect cell of claim 7, wherein the bacmid is a genome of AcMNPV (*Autographa californica* nucleopolyhedrovirus) or BmNPV (*Bombyx mori* nucleopolyhedrovirus).

9. A mass production method of a foreign target protein, the method including:
   a) cloning a foreign target protein coding nucleotide sequence into the recombinant transition vector of claim 1; and
   b) introducing bacmid and the cloned recombinant transition vector into an insect cell.

* * * * *

SEQUENCE LISTING

<160> NUMBER OF SEQ ID NOS: 9

<210> SEQ ID NO 1
<211> LENGTH: 483
<212> TYPE: DNA
<213> ORGANISM: Artificial Sequence
<220> FEATURE:
<223> OTHER INFORMATION: homologous region 5

<400> SEQUENCE: 1
cgcgtaaaac acaatcaagt atgagtcata agctgatgtc atgttttgca cacggctcat      60
aaccgaactg gctttacgag tagaattcta cttgtaacgc acgatcagtg gatgatgtca     120
tttgtttttc aaatcgagat gatgtcatgt tttgcacacg gctcataaac tcgctttacg     180
agtagaattc tacgtgtaac gcacgatcga ttgatgagtc atttgttttg caatatgata     240
tcatacaata tgactcattt gttttcaaa accgaacttg atttacgggt agaattctac      300
ttgtaaagca caatcaaaaa gatgatgtca tttgtttttc aaaactgaac tcgctttacg     360
agtagaattc tacgtgtaaa acacaatcaa gaaatgatgt catttgttat aaaaataaaa     420
gctgatgtca tgttttgcac acggctcata accgaactcg ctttacgggt agaattctac     480
gcg                                                                    483

<210> SEQ ID NO 2
<211> LENGTH: 40
<212> TYPE: DNA
<213> ORGANISM: Artificial Sequence
<220> FEATURE:
<223> OTHER INFORMATION: Burst sequence

<400> SEQUENCE: 2
ctgttttcgt aacagttttg taataaaaaa acctataaat                            40

<210> SEQ ID NO 3
<211> LENGTH: 329
<212> TYPE: DNA
<213> ORGANISM: Artificial Sequence
<220> FEATURE:
<223> OTHER INFORMATION: vp39 promoter sequence

<400> SEQUENCE: 3
gtcttgtaag gcagtttgat ttctttgctc tctctccaca ccagcggcac caacgcgttg      60
gtatctttag gccaataaac aaattttttg tgtttggaat tagtcttttt cacgcttgat     120
attatgttat tgcaagcgct ctgaataggt atacgagtgc gaaagccgtt ttcgtcgtac     180
aaatcgaaat attgttgtgc cagcgaataa ttaggaacaa tataagaatt taaaatttta     240
tacaacaaat cttggctaaa atttattgaa taagagattt ctttctcaat cataaaattg     300
ccgtggtcca tatttataac ggcaacaat                                       329

<210> SEQ ID NO 4
<211> LENGTH: 59
<212> TYPE: DNA
<213> ORGANISM: Artificial Sequence
<220> FEATURE:
<223> OTHER INFORMATION: polyhedrin gene promotor sequence

<400> SEQUENCE: 4
caaataaata agtattttac tgttttcgta acagttttgt aataaaaaaa cctataaat      59

<210> SEQ ID NO 5
<211> LENGTH: 26

```
<212> TYPE: DNA
<213> ORGANISM: Artificial Sequence
<220> FEATURE:
<223> OTHER INFORMATION: ORF603 specific primer sequence

<400> SEQUENCE: 5
ggtaccatat atagttgctg atggga                                          26

<210> SEQ ID NO 6
<211> LENGTH: 25
<212> TYPE: DNA
<213> ORGANISM: Artificial Sequence
<220> FEATURE:
<223> OTHER INFORMATION: EGFP specific primer sequence

<400> SEQUENCE: 6
gagctcttac ttgtacagct cgtcc                                           25

<210> SEQ ID NO 7
<211> LENGTH: 24
<212> TYPE: DNA
<213> ORGANISM: Artificial Sequence
<220> FEATURE:
<223> OTHER INFORMATION: mini-F  specific forward primer

<400> SEQUENCE: 7
atgttcagaa tgaaactcat ggaa                                            24

<210> SEQ ID NO 8
<211> LENGTH: 23
<212> TYPE: DNA
<213> ORGANISM: Artificial Sequence
<220> FEATURE:
<223> OTHER INFORMATION: mini-F  specific reverse primer

<400> SEQUENCE: 8
ttatctaatc tcccagcgtg gtt                                             23

<210> SEQ ID NO 9
<211> LENGTH: 5538
<212> TYPE: DNA
<213> ORGANISM: Artificial Sequence
<220> FEATURE:
<223> OTHER INFORMATION: pBacPAK9 vector sequence

<400> SEQUENCE: 9
aacggctccg cccactatta atgaaattaa aaattccaat tttaaaaaac gcagcaagag      60
aaacatttgt atgaaagaat gcgtagaagg aaagaaaaat gtcgtcgaca tgctgaacaa     120
caagattaat atgcctccgt gtataaaaaa atattgaac gatttgaaag aaaacaatgt     180
accgcgcggc ggtatgtaca ggaagaggtt tatactaaac tgttacattg caaacgtggt     240
ttcgtgtgcc aagtgtgaaa accgatgttt aatcaaggct ctgacgcatt tctacaacca     300
cgactccaag tgtgtgggtg aagtcatgca tcttttaatc aaatcccaag atgtgtataa     360
accaccaaac tgccaaaaaa tgaaaactgt cgacaagctc tgtccgtttg ctggcaactg     420
caagggtctc aatcctattt gtaattattg aataataaaa caattataaa tgtcaaattt     480 gtttttatt aacgatacaa accaaacgca acaagaacat ttgtagtatt atctataatt     540
gaaaacgcgt agttataatc gctgaggtaa tatttaaaat cattttcaaa tgattcacag     600
ttaatttgcg acaatataat tttatttca cataaactag acgccttgtc gtcttcttct     660
tcgtattcct tctctttttc attttctcc tcataaaaat taacatagtt attatcgtat     720
```

```
ccatatatgt atctatcgta tagagtaaat ttttgttgt cataaatata tatgtctttt    780 ttaatgggt gtatagtacc gctgcgcata gttttctgt aatttacaac agtgctattt     840
tctggtagtt cttcggagtg tgttgcttta attattaaat ttatataatc aatgaatttg   900
ggatcgtcgg ttttgtacaa tatgttgccg gcatagtacg cagcttcttc tagttcaatt  960
acaccatttt ttagcagcac cggattaaca taactttcca aaatgttgta cgaaccgtta  1020
aacaaaaaca gttcacctcc cttttctata ctattgtctg cgagcagttg tttgttgtta  1080
aaaataacag ccattgtaat gagacgcaca aactaatatc acaaactgga aatgtctatc  1140
aatatatagt tgctgatatc atggagataa ttaaaatgat aaccatctcg caaataaata  1200
agtattttac tgttttcgta acagttttgt aataaaaaaa cctataaata cggatcccgg  1260
gaattcgagc tcggtaccag atcttctaga ttcgaactcg aggcctgcag ggcggccgct  1320
taattaattg atccgggtta ttagtacatt tattaagcgc tagattctgt gcgttgttga  1380
tttacagaca attgttgtac gtatttaat aattcattaa atttataatc tttagggtgg   1440
tatgttagag cgaaaatcaa atgattttca gcgtctttat atctgaattt aaatattaaa  1500
tcctcaatag atttgtaaaa taggtttcga ttagtttcaa acaagggttg ttttccgaa    1560 ccgatggctg gactatctaa tggattttcg ctcaacgcca caaaacttgc caaatcttgt   1620
agcagcaatc tagctttgtc gatattcgtt tgtgttttgt tttgtaataa aggttcgacg  1680
tcgttcaaaa tattatgcgc ttttgtattt ctttcatcac tgtcgttagt gtacaattga  1740
ctcgacgtaa acacgttaaa taaagcttgg acatatttaa catcggcgt gttagcttta   1800 ttaggccgat tatcgtcgtc gtcccaaccc tcgtcgttag aagttgcttc cgaagacgat  1860
tttgccatag ccacacgacg cctattaatt gtgtcggcta acacgtccgc gatcaaattt  1920
gtagttgagc tttttggaat tatttctgat tgcgggcgtt tttgggcggg tttcaatcta  1980
actgtgcccg attttaattc agacaacacg ttagaaagcg atggtgcagg cggtggtaac  2040
atttcagacg gcaaatctac taatggcggc ggtggtggag ctgatgataa atctaccatc  2100
ggtggaggcg caggcggggc tggcggcgga ggcggaggcg gaggtggtgg cggtgatgca  2160
gacggcggtt taggctcaaa tgtctcttta ggcaacacag tcggcacctc aactattgta  2220
ctggtttcgg gcgccgtttt tggtttgacc ggtctgagac gagtgcgatt ttttcgttt    2280 ctaatagctt ccaacaattg ttgtctgtcg tctaaaggtg cagcgggttg aggttccgtc  2340
ggcattggtg gagcgggcgg caattcagac atcgatggtg gtggtggtgg tggaggcgct  2400
ggaatgttag gcacgggaga aggtggtggc ggcggtgccg ccggtataat tgttctggt   2460 ttagtttgtt cgcgcacgat tgtgggcacc ggcgcaggcg ccgctggctg cacaacggaa  2520
ggtcgtctgc ttcgaggcag cgcttggggt ggtggcaatt caatattata attggaatac  2580
aaatcgtaaa aatctgctat aagcattgta atttcgctat cgtttaccgt gccgatattt  2640
aacaaccgct caatgtaagc aattgtattg taaagagatt gtctcaagct cggatcgatc  2700
ccgcacgccg ataacaagcc ttttcatttt tactacagca ttgtagtggc gagacacttc  2760
gctgtcgtcg cctgatgcgg tatttttctcc ttacgcatct gtgcggtatt tcacaccgca  2820
tacgtcaaag caaccatagt acgcgccctg tagcggcgca ttaagcgcgg cgggtgtggt  2880
ggttacgcgc agcgtgaccg ctacacttgc cagcgcccta gcgcccgctc ctttcgcttt  2940
cttcccttcc tttctcgcca cgttcgccgg ctttccccgt caagctctaa atcgggggct  3000 cccctttaggg ttccgattta gtgctttacg gcacctcgac cccaaaaaac ttgatttggg  3060
tgatggttca cgtagtgggc catcgccctg atagacggtt tttcgccctt tgacgttgga  3120
```

```
gtccacgttc tttaatagtg gactcttgtt ccaaactgga acaacactca accctatctc    3180
gggctattct tttgatttat aagggatttt gccgatttcg gcctattggt taaaaaatga    3240
gctgatttaa caaaaattta acgcgaattt taacaaaata ttaacgttta caattttatg    3300
gtgcactctc agtacaatct gctctgatgc cgcatagtta agccagcccc gacacccgcc    3360
aacacccgct gacgcgccct gacgggcttg tctgctcccg gcatccgctt acagacaagc    3420
tgtgaccgtc tccgggagct gcatgtgtca gaggttttca ccgtcatcac cgaaacgcgc    3480
gagacgaaag ggcctcgtga tacgcctatt tttataggtt aatgtcatga taataatggt    3540
ttcttagacg tcaggtggca cttttcgggg aaatgtgcgc ggaacccta tttgtttatt    3600 tttctaaata cattcaaata tgtatccgct catgagacaa taaccctgat aaatgcttca    3660
ataatattga aaaaggaaga gtatgagtat tcaacatttc cgtgtcgccc ttattccctt    3720
ttttgcggca ttttgccttc ctgttttgc tcacccagaa acgctggtga agtaaaaga    3780 tgctgaagat cagttgggtg cacgagtggg ttacatcgaa ctggatctca acagcggtaa    3840
gatccttgag agttttcgcc ccgaagaacg ttttccaatg atgagcactt ttaaagttct    3900
gctatgtggc gcggtattat cccgtattga cgccgggcaa gagcaactcg gtcgccgcat    3960
acactattct cagaatgact tggttgagta ctcaccagtc acagaaaagc atcttacgga    4020
tggcatgaca gtaagagaat tatgcagtgc tgccataacc atgagtgata acactgcggc    4080
caacttactt ctgacaacga tcggaggacc gaaggagcta accgcttttt tgcacaacat    4140
gggggatcat gtaactcgcc ttgatcgttg ggaaccggag ctgaatgaag ccataccaaa    4200
cgacgagcgt gacaccacga tgcctgtagc aatggcaaca acgttgcgca aactattaac    4260
tggcgaacta cttactctag cttcccggca caattaata gactggatgg aggcggataa    4320
agttgcagga ccacttctgc gctcggccct tccggctggc tggtttattg ctgataaatc    4380
tggagccggt gagcgtgggt ctcgcggtat cattgcagca ctggggccag atggtaagcc    4440
ctcccgtatc gtagttatct acacgacggg gagtcaggca actatggatg aacgaaatag    4500
acagatcgct gagataggtg cctcactgat taagcattgg taactgtcag accaagttta    4560
ctcatatata ctttagattg atttaaaact tcatttttaa tttaaaagga tctaggtgaa    4620
gatccttttt gataatctca tgaccaaaat cccttaacgt gagttttcgt tccactgagc    4680
gtcagacccc gtagaaaaga tcaaaggatc ttcttgagat cctttttttc tgcgcgtaat    4740
ctgctgcttg caaacaaaaa aaccaccgct accagcggtg gtttgtttgc cggatcaaga    4800
gctaccaact cttttccga aggtaactgg cttcagcaga gcgcagatac caaatactgt    4860
tcttctagtg tagccgtagt taggccacca cttcaagaac tctgtagcac cgcctacata    4920
cctcgctctg ctaatcctgt taccagtggc tgctgccagt ggcgataagt cgtgtcttac    4980
cgggttggac tcaagacgat agttaccgga taaggcgcag cggtcgggct gaacggggg    5040 ttcgtgcaca cagcccagct tggagcgaac gacctacacc gaactgagat acctacagcg    5100
tgagctatga gaaagcgcca cgcttcccga agggagaaag gcggacaggt atccggtaag    5160
cggcagggtc ggaacaggag agcgcacgag ggagcttcca gggggaaacg cctggtatct    5220
ttatagtcct gtcgggtttc gccacctctg acttgagcgt cgatttttgt gatgctcgtc    5280
aggggggcgg agcctatgga aaaacgccag caacgcggcc ttttacggt tcctggcctt    5340 ttgctggcct tttgctcaca tgttctttcc tgcgttatcc cctgattctg tggataaccg    5400
tattaccgcc tttgagtgag ctgataccgc tcgccgcagc cgaacgaccg agcgcagcga    5460
```

```
gtcagtgagc gaggaagcgg aagagcgccc aatacgcaaa ccgcctctcc ccgcgcgttg    5520
gccgattcat taatgcag                                                  5538
```